(12) United States Patent
Holland et al.

(10) Patent No.: US 11,047,997 B2
(45) Date of Patent: Jun. 29, 2021

(54) ROTATING SCATTER MASK FOR DIRECTIONAL RADIATION DETECTION AND IMAGING

(71) Applicant: US Gov't as represented by Secretary of Air Force, Wright-Patterson AFB, OH (US)

(72) Inventors: Darren Holland, Springfield, OH (US); Robert Olesen, Fairborn, OH (US); Larry Burggraf, Washington Township, OH (US); Buckley O'Day, Dunn Loring, VA (US); James Bevins, Bellbrook, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 17/007,063

(22) Filed: Aug. 31, 2020

(65) Prior Publication Data
US 2020/0393580 A1   Dec. 17, 2020

Related U.S. Application Data

(63) Continuation-in-part of application No. 16/812,844, filed on Mar. 9, 2020.
(Continued)

(51) Int. Cl.
*G01T 7/00* (2006.01)
*G06N 3/04* (2006.01)
(Continued)

(52) U.S. Cl.
CPC .............. *G01T 7/00* (2013.01); *G01T 1/2018* (2013.01); *G01T 3/06* (2013.01); *G06N 3/04* (2013.01); *G06N 3/08* (2013.01); *A61B 6/4258* (2013.01)

(58) Field of Classification Search
None
See application file for complete search history.

(56) References Cited

U.S. PATENT DOCUMENTS

| | | | |
|---|---|---|---|
| 2015/0106316 A1* | 4/2015 | Birdwell | G06N 3/02 706/33 |
| 2020/0292720 A1* | 9/2020 | Olesen | G01T 1/15 |

* cited by examiner

*Primary Examiner* — Edwin C Gunberg
(74) *Attorney, Agent, or Firm* — AFMCOL/JAZ; David E. Franklin

(57) ABSTRACT

A radiation imaging system images a distributed source of radiation from an unknown direction by rotating a scatter mask around a central axis. The scatter mask has a pixelated outer surface of tangentially oriented, flat geometric surfaces that are spherically varying in radial dimension that corresponds to a discrete amount of attenuation. Rotation position of the scatter mask is tracked as a function of time. Radiation counts from gamma and/or neutron radiation are received from at least one radiation detector that is positioned at or near the central axis. A rotation-angle dependent detector response curve (DRC) is generated based on the received radiation counts. A reconstruction algorithm for distributed radiation source(s) and/or localized source(s) are applied based on the tracked rotation position and prior characterization of the detector response for a given scatter mask. A two-dimensional image with relative orientation and source distribution is generated from the measured DRC.

8 Claims, 10 Drawing Sheets

Related U.S. Application Data

(60) Provisional application No. 62/986,892, filed on Mar. 9, 2020, provisional application No. 62/816,435, filed on Mar. 11, 2019, provisional application No. 62/816,451, filed on Mar. 11, 2019.

(51) Int. Cl.
*G01T 1/20* (2006.01)
*G01T 3/06* (2006.01)
*G06N 3/08* (2006.01)
*A61B 6/00* (2006.01)

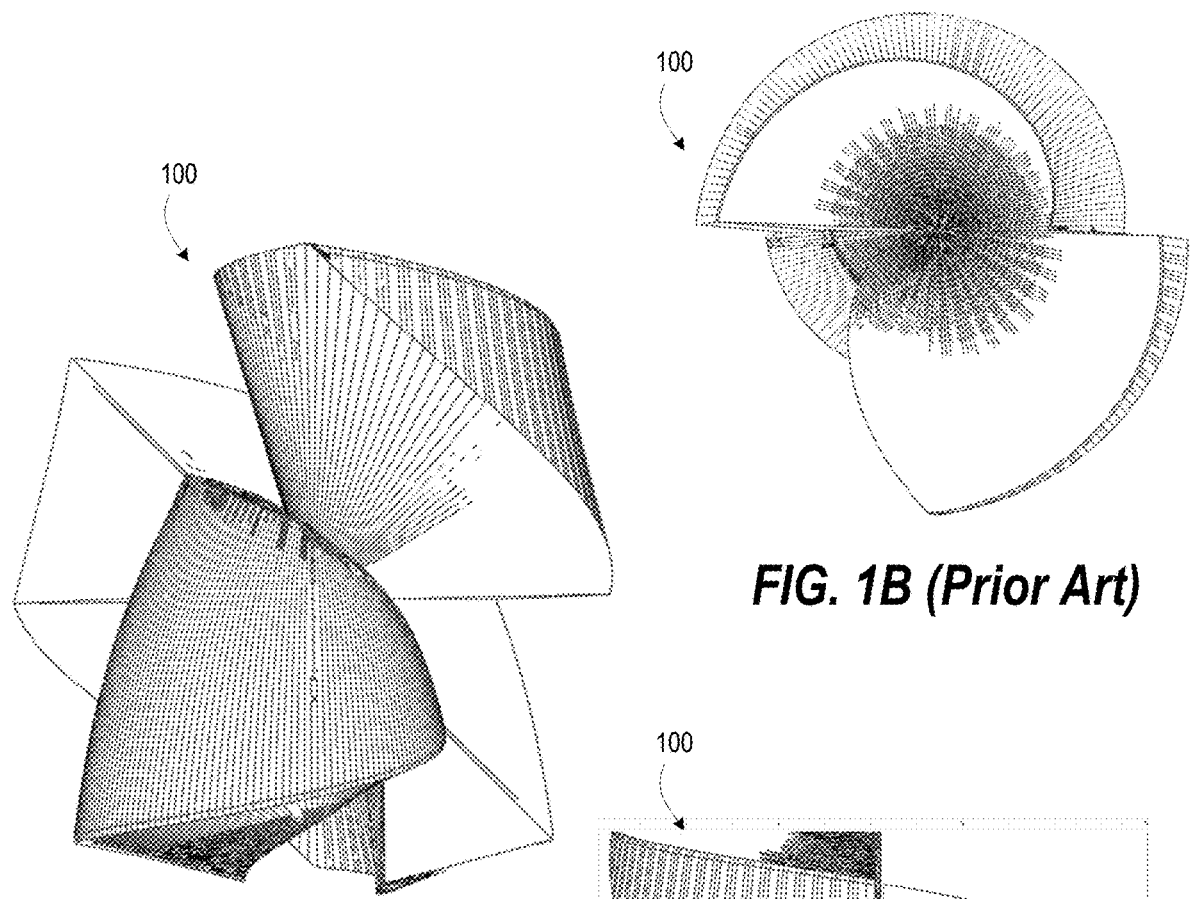
FIG. 1B (Prior Art)
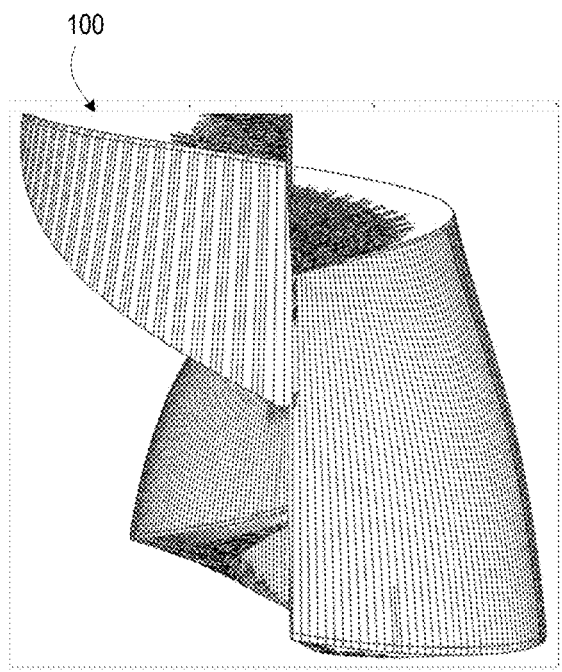
FIG. 1A (Prior Art)
FIG. 1C (Prior Art)

ROTATING SCATTER MASK FOR DIRECTIONAL RADIATION DETECTION AND IMAGING

CROSS-REFERENCE TO RELATED APPLICATIONS

This application claims the benefit of priority under 35 U.S.C. § 119(e) to U.S. Provisional Application Ser. No. 63/003,950 entitled "Rotating Scatter Mask Design Classes for Directional Radiation Detection and Imaging", filed 2 Apr. 2020, the contents of which are incorporated herein by reference in their entirety.

This application is a continuation-in-part under 5 U.S.C. § 120 to U.S. patent application Ser. No. 16/812,844 entitled "An Efficient, Dual-particle Directional Detection System using a Rotating Scatter Mask," filed 9 Mar. 2020, which in turn claimed priority under 35 U.S.C. § 119(e) to three (3) U.S. Provisional Applications:

(i) Ser. No. 62/816,451 entitled "An Efficient, Dual-particle Directional Detection System using a Rotating Scatter Mask," filed 11 Mar. 2019;

(ii) Ser. No. 62/816,435 entitled "Rotating Scatter Mask Design Classes for Directional Radiation Detection and Imaging", filed 11 Mar. 2019; and (iii) Ser. No. 62/986,892 entitled "Rotating Scatter Mask Design Classes for Directional Radiation Detection and Imaging", filed 9 Mar. 2020, the contents of all of which, and the references cited therein, are hereby incorporated herein by reference in their entirety.

ORIGIN OF THE INVENTION

The invention described herein was made by employees of the United States Government and may be manufactured and used by or for the Government of the United States of America for governmental purposes without the payment of any royalties thereon or therefore.

BACKGROUND

1. Technical Field

The present disclosure generally relates to testing apparatus and methods of detecting and imaging sources of gamma and/or neutron radiation.

2. Description of the Related Art

There has been a long and growing interest in portable, real-time radiation imaging systems within the nuclear safety and security field. Radioactive sources can be found in many peaceful applications, ranging from medicine to power generation. Radioactive material localization is particularly important for nuclear power facilities due to the storage of radioactive waste and increased number of plants requiring characterization in preparation for decommissioning (see Laraia, Nuclear Decommissioning: Planning, Execution and Decommissioning, Woodhead Publishing, (2012), which is hereby incorporated by reference in its entirety). Accurate monitoring of these sources maintains positive control of potential contamination and minimizes the associated health risks for inspectors and personnel. Localization also significantly improves nuclear security by enabling interdiction of illicit nuclear material and providing more precise details on the composition and location of the material (see Jovanovic et al., Active Interrogation in Nuclear Security: Science, Technology and Systems, Springer Publishing, (2018), which is hereby incorporated by reference in its entirety). Sites may also be monitored using these systems for treaty verification purposes to detect any unwarranted changes in storage and production (see Hausladen et al., The deployable fast-neutron coded-aperture imager: Demonstration of locating one or more sources in three dimensions, Oak Ridge National Laboratory, Oak Ridge, Tenn. (2013), which is hereby incorporated by reference in its entirety).

Coded-aperture imaging and Compton cameras have become popular devices among modern gamma-ray imagers (see H. A. Hamrashdi, S. D. Monk, D. Cheneler, "Passive gamma-ray and neutron imaging systems for national security and nuclear non-proliferation in controlled and uncontrolled detection areas: Review of past and current status," Sensors, vol. 19, no. 11, (2019) and Vetter et al., Gamma-ray imaging methods, Tech. rep., Lawrence Livermore National Lab, Livermore, Calif. (2006), each of which is hereby incorporated by reference in its entirety). However, coded-aperture imaging is limited in field-of-view (FOV), which increases the time required to survey surrounding areas and is often composed of an array of attenuating masks and scintillating detectors, inhibiting the portability of the device (see Cieslak et al., Coded-aperture imaging systems: Past, present and future development—a review, Radiation Measurements, 92 (2016) 59-71, which is hereby incorporated by reference in its entirety), although recent developments have shown some improvements through alternative detector arrangements and reconstruction algorithms (see Hellfeld et al., A Spherical Active Coded Aperture for $4\pi$ Gamma-Ray Imaging, IEEE Transactions on Nuclear Science, 64 (11) (2017) 2837-2842 and Zhang et al., Reconstruction method for gamma-ray coded-aperture imaging based on convolutional neural network, Nucl. Instrum. Methods Phys. Res. A, 937 (2019) 41-51, each of which is hereby incorporated by reference in its entirety). Compton cameras benefit from a full $4\pi$-FOV and being highly portable, but they have inherently reduced efficiencies due to the requirement for detecting correlated events and may not be used for imaging neutron sources (see Kim et al., Large-Area Compton Camera for High-Speed and 3-D Imaging, IEEE Transactions on Nuclear Science 65 (11) (2018) 2817-2822 and McCleskey et al., Evaluation of a multistage CdZnTe Compton camera for prompt imaging for proton therapy, Nucl. Instrum. Methods Phys. Res. A, 785 (2015) 163-169, each of which is hereby incorporated by reference in its entirety). All these methods share a common requirement for high channel count for accurate imaging and are often complex, costly systems.

Advanced neutron scatter cameras are currently being investigated that address many of these problems (see Goldsmith et al. A compact neutron scatter camera for field deployment, Review of Scientific Instruments, 87 (8) (2016), which is hereby incorporated by reference in its entirety). Another recent advancement is the development of a Single-Volume Neutron Scatter Camera (SVNSC) (see K. Weinfurther, Model-based design evaluation of a compact, high-efficiency neutron scatter camera, Nucl. Instrum. Methods Phys. Res. A, 883 (2018) 115-135 and J. Braverman, Single-Volume Neutron Scatter Camera for High-Efficiency Neutron Imaging and Spectroscopy, arXiv:1802.05261, each of which is hereby incorporated by reference in its entirety). Although these approaches obtain a $4\pi$ steradian FOV, they are complicated to operate as it requires signal processing electronics with a high time resolution, many channels of data, and are relatively costly.

Fitzgerald introduced the rotating scatter mask (RSM) 100 shown in FIGS. 1A-1C to overcome many of these current limitations with the ultimate goal of developing a simple, efficient, portable, directional detection system with a large FOV (see FitzGerald, A rotating scatter mask for inexpensive gamma-ray imaging in orphan source search: Simulation results, IEEE Trans. Nucl. Sci., 62 (1) (2015) 340-348, which is hereby incorporated by reference in its entirety). The RSM concept utilizes a rotating mask around a single detector to attenuate and scatter, not collimate, radiation and determine the direction of a gamma-ray source. By using single event detection, the system offers improved efficiency over Compton cameras and reduced size over coded-apertures, while significantly reducing the complexity and cost. The use of a rotating mask extends the FOV to nearly-4π and reduces the system efficiency only through mask attenuation, some of which can be recovered through detected mask-scatter events. Unlike the masks used in coded apertures, which project an image onto an array of detectors, the RSM is more closely related to Bonner spheres, attenuating the particles before they reach the detector. However, unlike a Bonner sphere, the mask is geometrically complex so that the attenuation varies based on the source direction.

FitzGerald's design generates some directional degeneracies that result in nearly identical detection system response for multiple directions. In imaging, where the source may be distributed, the degeneracy causes the problem to be underdefined such that an infinite number of solutions (images) exist that produce the same detector response. FitzGerald noted "phantom" sources, image artifacts, and unresolved source shapes. Additionally, the Fitzgerald design, at 26 kg, was too large to be considered truly portable.

Logan et al. (see Logan, Monte Carlo and experimental analysis of a novel directional rotating scatter mask gamma detection system, Nucl. Instrum. Methods Phys. Res. A, 947 (2019) 162698, which is hereby incorporated by reference in its entirety) conducted the first experiments using FitzGerald's design and demonstrated statistical agreement between the simulations and experiments when using gamma point sources. This work proved the existence of a high degree of similarity among spatially separated detector responses. Thus, FitzGerald's design is unable to accurately or reliably image a radiation source's spatial distribution.

Many algorithms exist in literature throughout a variety of fields and applications that can resolve an image based on the system's response. For imaging a radiation source, the ability to demonstrate the reconstruction accuracy depends on both the invention's characteristics and algorithm's ability to find the correct solution. Two such image reconstruction algorithms that can combine with the invention to create a true imaging device are maximum-likelihood expectation-maximization (ML-EM) and the regenerative neural network (ReGeNN).

SUMMARY

The present innovation overcomes the foregoing problems and other shortcomings, drawbacks, and challenges of imaging distributed radiation sources from an unknown direction. While the present innovation will be described in connection with certain embodiments, it will be understood that the invention is not limited to these embodiments. To the contrary, this invention includes all alternatives, modifications, and equivalents as may be included within the spirit and scope of the present invention.

According to one aspect of the present innovation, a method provides imaging of a distributed source of radiation from an unknown direction. In one or more embodiments, the method includes rotating a scatter mask around a central axis. The scatter mask has a pixelated outer surface of tangentially oriented, flat geometric surfaces that are spherically varying in radial dimension from a central position of the central axis by a respective pseudo-random distance. The pseudo-random distance varies between a minimum distance and a maximum distance to provide a particular thickness that corresponds to a discrete amount of attenuation. The method includes tracking rotation position of the scatter mask as a function of time. The method includes receiving radiation counts from at least one radiation detector that is positioned at or near the central axis and that detects one or more of gamma radiation and neutron particle radiation. The method includes generating a rotation-angle dependent detector response curve (DRC) based on the received radiation counts. The method includes applying one or more of: (i) a reconstruction algorithm for one or more distributed radiation source(s); and (ii) one or more localized sources based on the tracked rotation position and prior characterization of the detector response for a given scatter mask. The method includes generating a two-dimensional image that is associated with a relative orientation and distribution of a source of radiation from the measured DRC.

According to one aspect of the present innovation, a radiation imaging system images distributed and localized sources of radiation from an unknown direction. In one or more embodiments, the radiation imaging system includes a scatter mask having a pixelated outer surface of tangentially oriented, flat geometric surfaces that are spherically varying in radial dimension from a central position of a central axis by a respective pseudo-random distance. The pseudo-random distance varies between a minimum distance and a maximum distance to provide a particular thickness that corresponds to a discrete amount of attenuation. The radiation imaging system includes at least one radiation detector that is positioned at the central axis and that detects one or more of gamma radiation and neutron particle radiation. The radiation imaging system includes a rotation system to rotate the scatter mask around the central axis. The radiation imaging system includes a controller that is communicatively coupled to the at least one radiation detector and the rotation system. The controller tracks rotation position of the scatter mask as a function of time. The controller receives radiation counts from at least one radiation detector that is positioned at or near the central axis and that detects one or more of gamma radiation and neutron particle radiation. The controller generates a rotation-angle dependent DRC based on the received radiation counts. The controller applies one or more of: (i) a reconstruction algorithm for one or more distributed radiation source(s); and (ii) one or more localized sources based on the tracked rotation position and prior characterization of the detector response for the scatter mask. The controller generates a two-dimensional image that is associated with a relative orientation and distribution of a source of radiation from the measured DRC.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 1A illustrates a first side view of a generally-known FitzGerald scatter mask;

FIG. 1B illustrates a top view of the generally-known FitzGerald scatter mask of FIG. 1A;

FIG. 1C illustrates a second side view orthogonal to the first side view of the generally-known FitzGerald scatter mask of FIG. 1A;

DETAILED DESCRIPTION

In one or more embodiments, a method and apparatus to localize or image a radiation source's spatial distribution is disclosed. An innovative Eigenvector rotating scatter mask (RSM) is combined with a dual-particle detector and data acquisition unit, a mechanism for rotating the invention, and hardware for collecting and analyzing the resulting data. Radiation passing though the RSM scatters and/or attenuates. As the innovative scatter mask rotates, unique geometry of the scatter mask produces a unique detected response dependent on position and spatial extent of a radiation source. Thus, a time and position dependent detection signal is the result. The associated analysis algorithm combines this signal with the mask rotation position information to expand the RSM concept into an imaging device through a robust neural network reconstruction algorithm. As a result, the present invention can accurately resolve complex, noisy source shapes, while avoiding "phantom" sources and image artifacts.

Figure 2A:
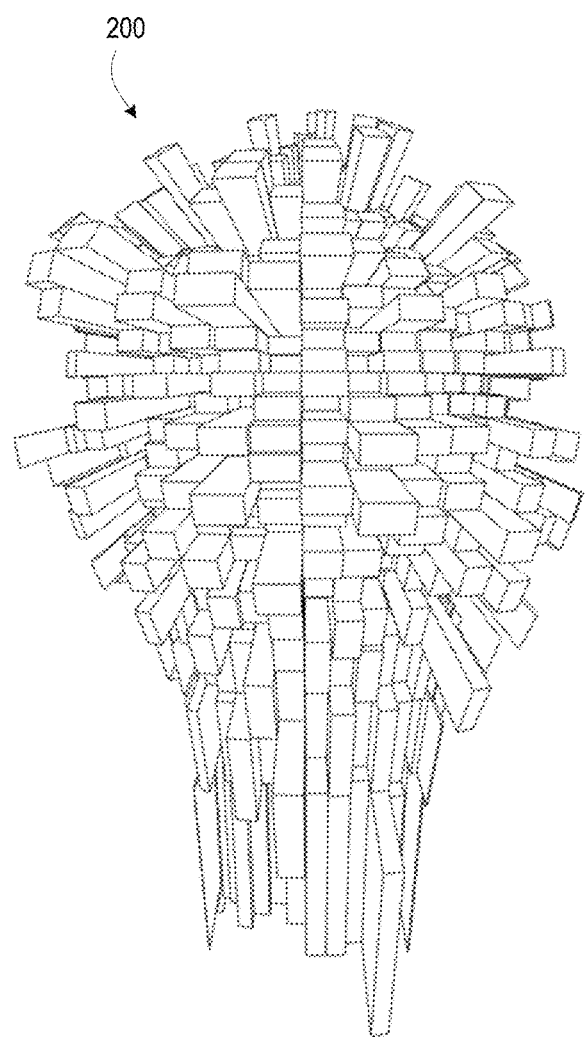
FIG. 2A illustrates a first side view of the Eigenvector-based scatter mask, according to one or more embodiments.
Figure 2B:
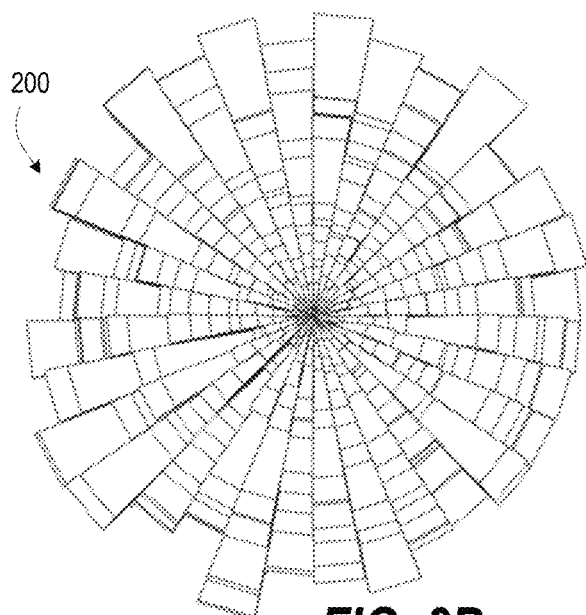
FIG. 2B illustrates a top view of the Eigenvector-based scatter mask of FIG. 2A, according to one or more embodiments.
Figure 2C:
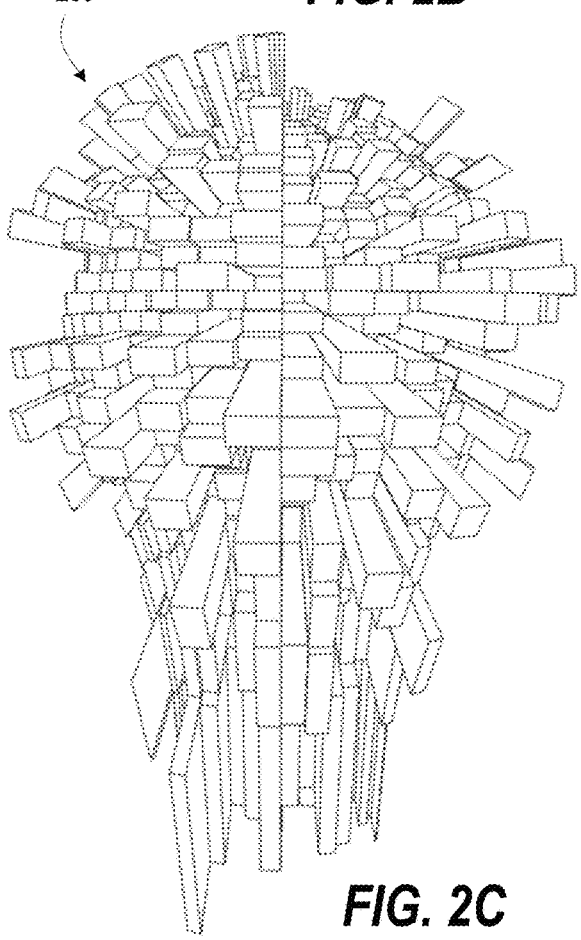
FIG. 2C illustrates a second side view orthogonal to the first side view of the Eigenvector-based scatter mask of FIG. 2A, according to one or more embodiments.

FIG. 2A illustrates a first side view of an Eigenvector RSM 200. FIG. 2B illustrates a top view of the Eigenvector RSM 200. FIG. 2C illustrates a second side view orthogonal to the first side view of the Eigenvector RSM 200. The Eigenvector RSM 200 is a geometrically varying mask 200 placed over a single detector or single detector system. The Eigenvector RSM 200 is rotated about the detector. By recording the number of counts detected as the mask rotates about the detector, a rotation-angle dependent detector response curve (DRC) is generated, which can be post-processed to retrieve the source's direction and spatial distribution. The Eigenvector RSM 200 enables a time-encoded directionally sensitive system that requires only a single detector.

Holland et al. (see Holland, Rotating scatter mask optimization for gamma source direction identification, Nucl. Instrum. Methods Phys. Res. A, 901 (2018) 104-111, which is hereby incorporated by reference in its entirety) introduced the Eigenvector approach to improve and minimize FitzGerald's directional degeneracies, resulting in the present invention.

For this application, it is desirable that the DRC associated with each initial source position be unique, i.e. orthogonal to all other curves associated with the other source positions. Let this curve be denoted $DRC_{i,j}$, where i=0, 1, . . . , p is the initial azimuthal angle θ index and j=0, 1, . . . , m is the initial polar angle Φ index relative to a reference location on the mask. Since the mask rotates, the $i^{th}$ DRC will be identical to $DRC_{g,j}$ shifted by g-i indices. A negative number corresponds to a shift to the left and a positive number a shift to the right. This property greatly impacts the mask design as any periodic vector with respect to the azimuthal direction will result in duplicate i and g DRCs. The duplication due to periodicity would result in perfect directional degeneracy and cause the imaging to fail for certain source directions.

The eigenvector approach creates and solves an eigenvalue problem based on a small number of parameters to generate a basis set, which may be used to define the more complex mask geometry. One benefit of reducing the number of parameters in the eigenvalue problem is that the geometry can be controlled by n parameters. For example, in one embodiment of the invention, using n=32 produced 960 separate mask geometry values. In general, a simple eigenvalue problem is comprised of a stiffness and normalized mass matrix. First, n k values are chosen, where k is the coupling constant analogous to a spring-mass coupling problem. These values are then placed in a stiffness matrix. This approach assumes there is additional coupling between nearby springs, which represents the spatial coupling among nearby polar angles on the RSM. Other coupling methods and more complex eigenvalue problems could be introduced, if desired.

Note that the k values chosen do not need to represent physical systems (e.g. negative stiffness values are acceptable). Thus, systems with positive, negative, and a combination of both k values apply.

Once the system is constructed, an eigenvalue problem is solved resulting in n orthonormal eigenvectors used to represent the geometry for an initial azimuthal position and all initial polar positions. If the first vector corresponds to planar motion (a cyclical vector, which would cause a degeneracy) it is not chosen. This elimination results in a matrix formed by eigenvectors 2 . . . m+1.

Next, the eigenvectors are made linearly dependent. This step reduces the amount of degeneracy among strongly similar DRCs, but increases the similarity with initially dissimilar DRCs. To introduce linear dependence, a modified Gram-Schmidt orthogonality approach is used. This approach subtracts the similar component of other shifted eigenvectors from the initially linearly independent basis. Various combinations of eigenvectors and shifts, are acceptable; however, a shift is required due to the initial orthogonality (otherwise there is no similar portion to subtract).

Next, the average of each new eigenvector is subtracted from the corresponding vector. Since mask material may only be added, the minimum value (plus a small, constant thickness) is added to the eigenvector to make all the thicknesses positive. Lastly, each eigenvector is normalized by the maximum vector value resulting in each vector having values greater than zero and less than one. Then, the vectors are scaled to a desired maximum thickness. These modified eigenvector values can be expressed in a 2D matrix, which represents the RSM geometry. Each entry corresponds to the mask thickness in a given azimuthal and polar direction.

The invention may be manufactured out of many materials with an adequate probability for gamma and neutron interactions. This flexibility allows the invention to apply to a wide range of radiation types and energies. However, some materials require thicker geometric features, which increases the size and weight, while reducing its portability. Common 3-D printing plastics have been found to perform well for imaging while reducing the system weight.

Figure 3A:
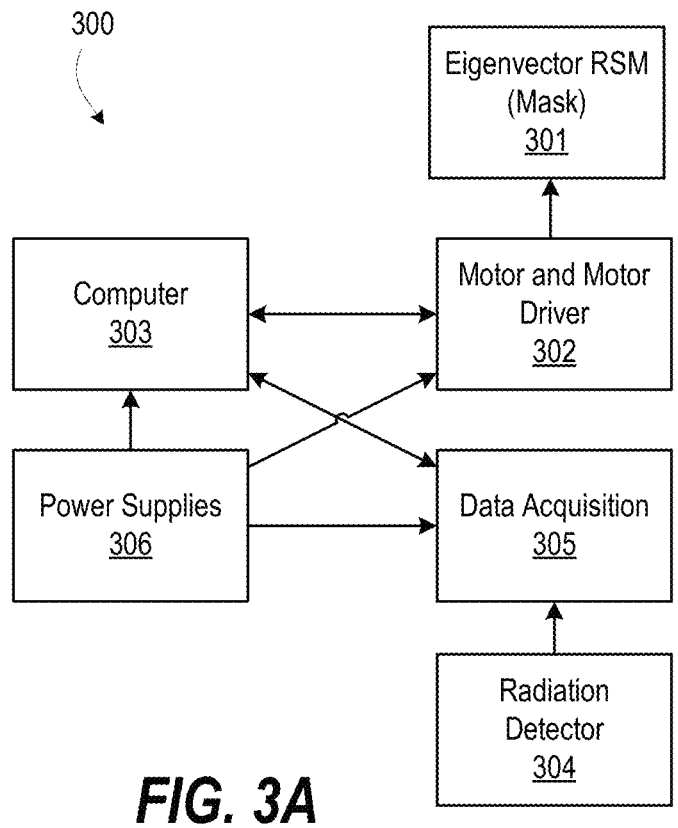
FIG. 3A is a functional block diagram of an example identification system that utilizes the Eigenvector-based scatter mask of FIG. 2A, according to one or more embodiments.

FIG. 3A shows that an identification system 300 incorporating one embodiment of the invention is composed of the Eigenvector RSM (mask) 301, a rotational motor system 302, a computer 303, and radiation detection electronics 304-305. Each of these components has a corresponding power supply 306. For instance, to identify a neutron and gamma source's direction (see Egner et al., Development of a Mixed-Radiation Directional Rotating Scatter Mask Detection System, Theses and Dissertations. (2019) 2357, which is hereby incorporated by reference in its entirety), a pulse-shape discriminating scintillator is mounted to a photodetector 304 connected to a digital data acquisition system (DAQ) 305. The detector and photodetector assembly are secured inside of a fixed detector support tube attached to the assembly box. The present invention is attached to a second support tube (the mask holder) surrounding the first tube, which contains the pulse shape discriminating scintillator and photodetector. The mask and mask holder are supported and rotated by two gears attached to a stepper motor coupled to an encoder ring 302. The motion of the stepper motor is controlled by a stepper driver 302 configured by a mounted Raspberry Pi or a personal computer 303. The DAQ, Raspberry Pi, stepper motor, and driver are powered either by rechargeable batteries or alternating current power 306.

Figure 3B:
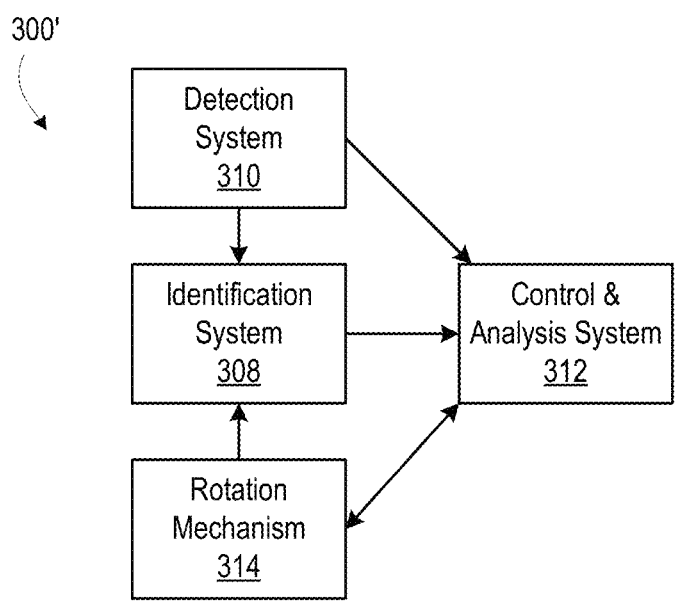
FIG. 3B is a functional block diagram of another example identification system that utilizes the Eigenvector-based scatter mask of FIG. 2A, according to one or more embodiments.

FIG. 3B depicts another example identification system 300'. A detection system 310 including the detector, associated electronics, and surrounding invention sends information to the identification system 308. At the same time, a control and analysis system 312 works in conjunction with a rotation mechanism 314 to set the correct position of the RSM shown in FIG. 2. The identification system 308 processes the detection information and position of the RSM shown in FIG. 2 to produce an image and updates the control and analysis system 312.

To function as an imager, the RSM is coupled with an analysis algorithm. The first potential algorithm, maximum-likelihood expectation-maximization (ML-EM), is based on a stochastic model for radiation emission and is frequently used for medical imaging and the previously mentioned coded-apertures (See T. K. Moon, The expectation-maximization algorithm, IEEE Signal Processing Magazine 13 (6) (1996) 47-60, which is hereby incorporated by reference in its entirety). When a smoothing prior is applied to ML-EM, finer details are often lost in the reconstructed image, but the overall shape is better represented. The resolution limitations are primarily driven by the neighborhood size used to calculate the smoothing penalty and the resolution of the measured detector response. However, realistic source distributions do not inherently correspond to images with the highest detection probability. Thus, traditional maximum likelihood estimates fail to accurately reconstruct most source images when using measurements from the present invention (See R. J. Olesen et al., Maximum likelihood reconstructions for rotating scatter mask imaging, Radiation Measurements, 137, (2020), 106441, which is hereby incorporated by reference in its entirety).

Figure 4A:
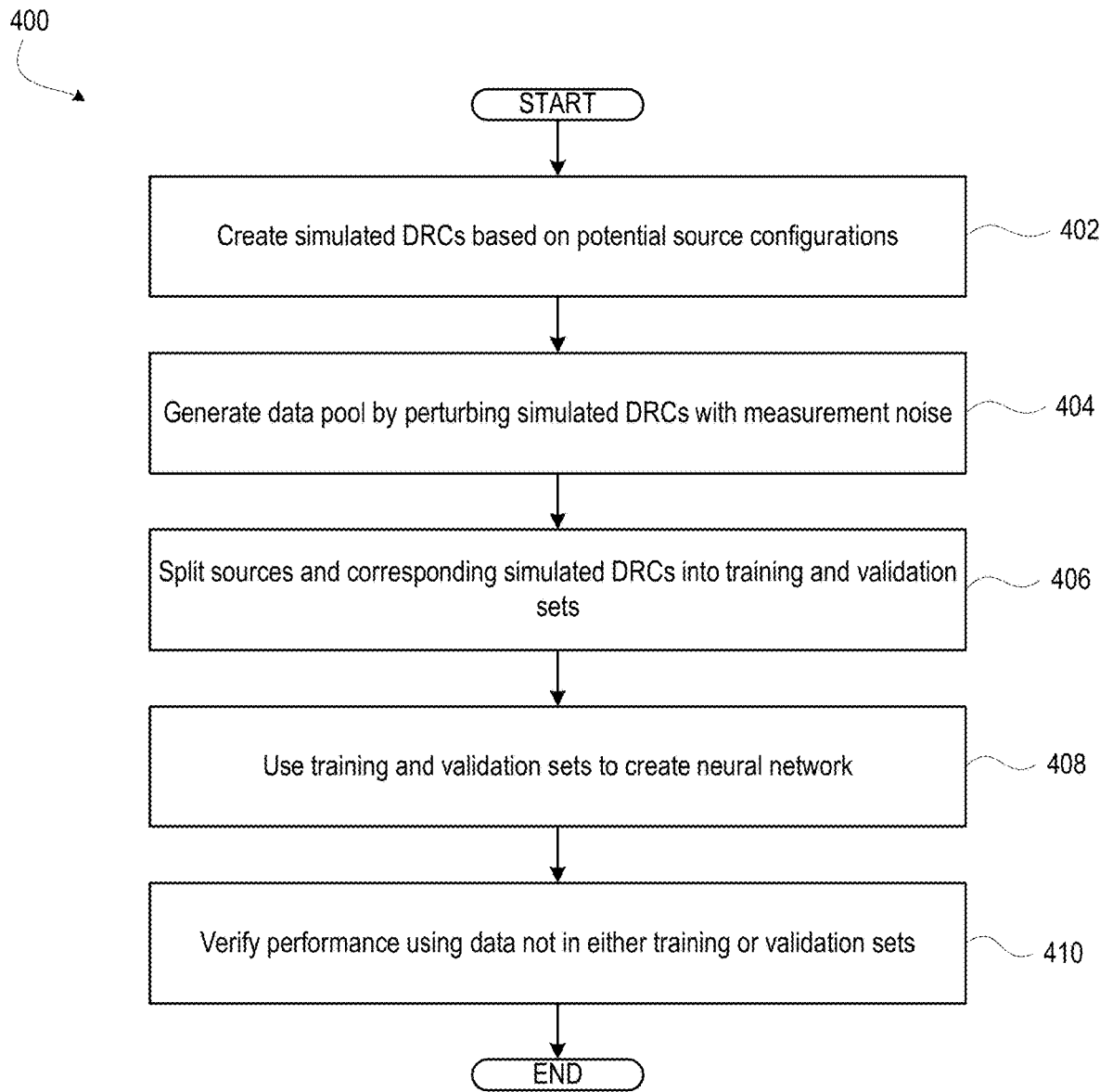
FIG. 4A presents a flow diagram of a method to generate the regenerative neural network (ReGeNN), according to one or more embodiments.

Modern machine learning algorithms are perfectly suited for this task as the reconstruction algorithm can be trained on application-specific expected source distributions. A regenerative neural network (ReGeNN) was developed and trained on realistic source distributions, positively biasing "real images" and suppressing noisy or unlikely distributions. FIG. 4A presents a flow diagram of method 400 for the ReGeNN creation process. First, expected source distributions are created and DRCs simulated using a radiation transport code (block 402). The DRC input is first normalized to a sum of one; this is necessary to train the network on shape rather than source activity. Then, artificial noise was introduced in the training data to account for the statistical measurement uncertainty and prevent over-fitting to the training data (block 404). Using this data, a neural network is created (block 408). In one embodiment, the ReGeNN was trained and validated using 514,080 noisy DRCs. The last step is to verify the network using data that was not in the training nor validation set (block 410). Then method 400 ends.

Figure 4B:
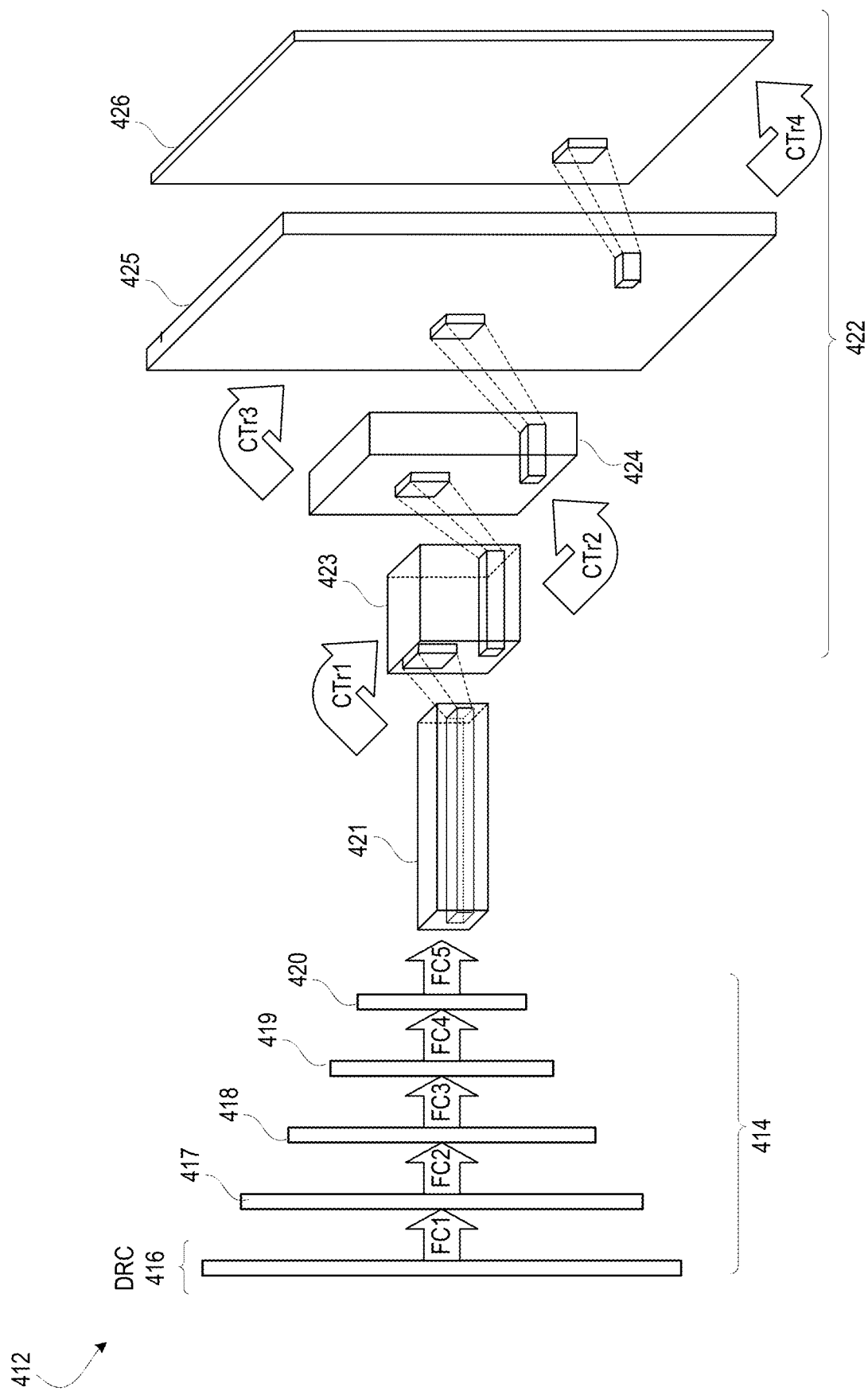
FIG. 4B is a graphical representation of the ReGeNN encoding and decoding process for one embodiment of the invention.

FIG. 4B is a graphical representation of a neural network architecture for one embodiment. The first half 414 of the ReGeNN 412 acts as an encoder, condensing a one-dimensional (1D) DRC into a matrix 421 that, theoretically, contains the most important information about the source's distribution. In one or more embodiments, DRC vector 416 that is 1×360 is processed by first fully connected network (FC1) to produce vector 417 that is 1×256. Vector 417 is processed by second fully connected network (FC2) to produce vector 418 that is 1×128. Vector 418 is processed by third fully connected network (FC3) to produce vector 419 that is 1×64. Vector 419 is processed by fourth fully connected network (FC4) to produce vector 420 that is 1×32. Vector 420 is processed by fifth fully connected network (FC5) to produce encoded vector 421 that is 9×9×256. The second half 422 of ReGeNN 412 acts as a "deconvolution", upscaling the encoded matrix 421 into a two-dimensional (2D) image and deconvolving until a final source image 426 is reconstructed. In one or more embodiments, encoded vector 421 undergoes first convolutional transpose (CTr1) to become first interim result 423 that is 18×21×128. First interim result 423 undergoes second convolutional transpose (CTr2) to become second interim result 424 that is 36×21× 64. Second interim result 424 undergoes third convolutional transpose (CTr3) to become third interim result 425 that is 72×21×32. Third interim result 425 undergoes fourth convolutional transpose (CTr4) to become final source image 426 that is 360×21×1. The final source image 426, like the input, is normalized to relative activity, ranging from zero to one. The same architecture may be used for other imaging devices, with the encoder portion changed to match the signal's dimensions.

Figure 4C:
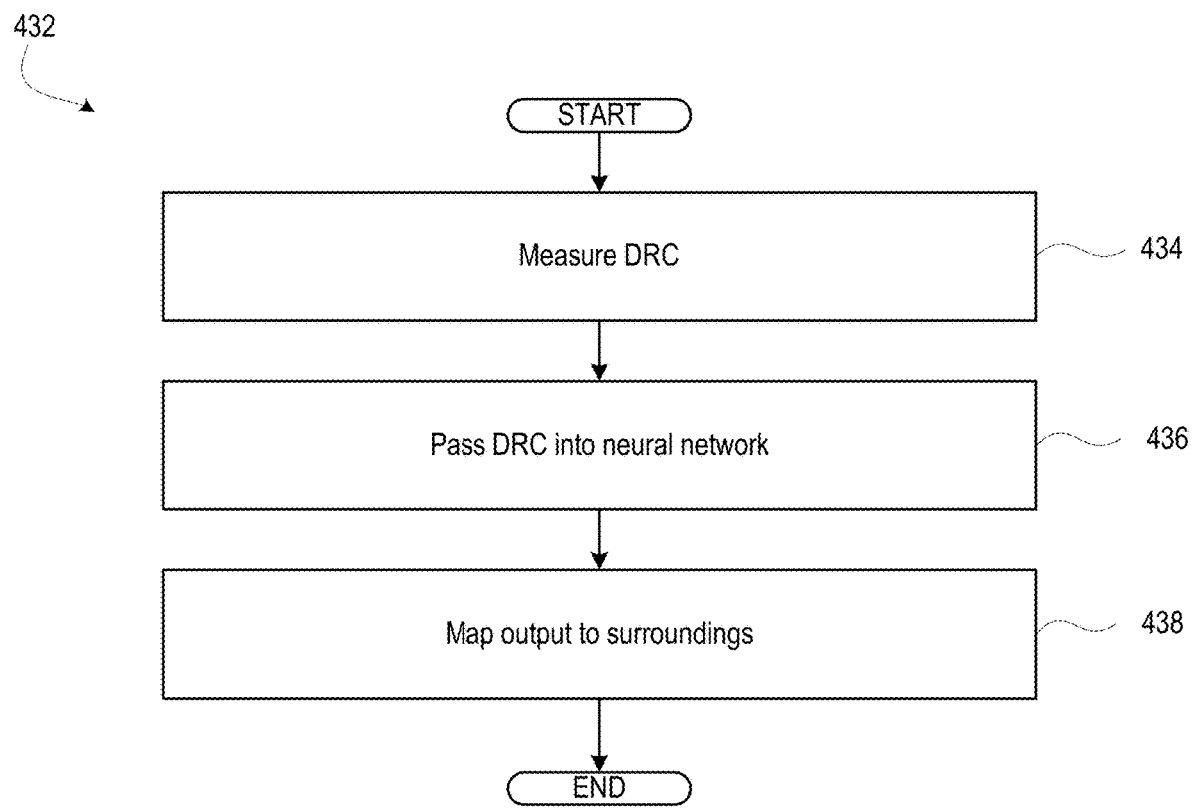
FIG. 4C presents a flow diagram of a method to generate the reconstructed image, according to one or more embodiments.

FIG. 4C depicts the process 432 for applying the HCNN created by the training process (method 400 of FIG. 4A) to simulated or experimental measurements. First, experimental or simulated DRCs are recorded (block 434). Then, the DRC is passed into the neural network (block 436). If desired, the image output can then be mapped onto an image of a user's surrounding (block 438). The ReGeNN-based reconstruction algorithm showed a significant improvement in the reconstruction accuracy compared to traditional ML-EM approaches, even when statistical noise was included in the measurements.

Figure 5:
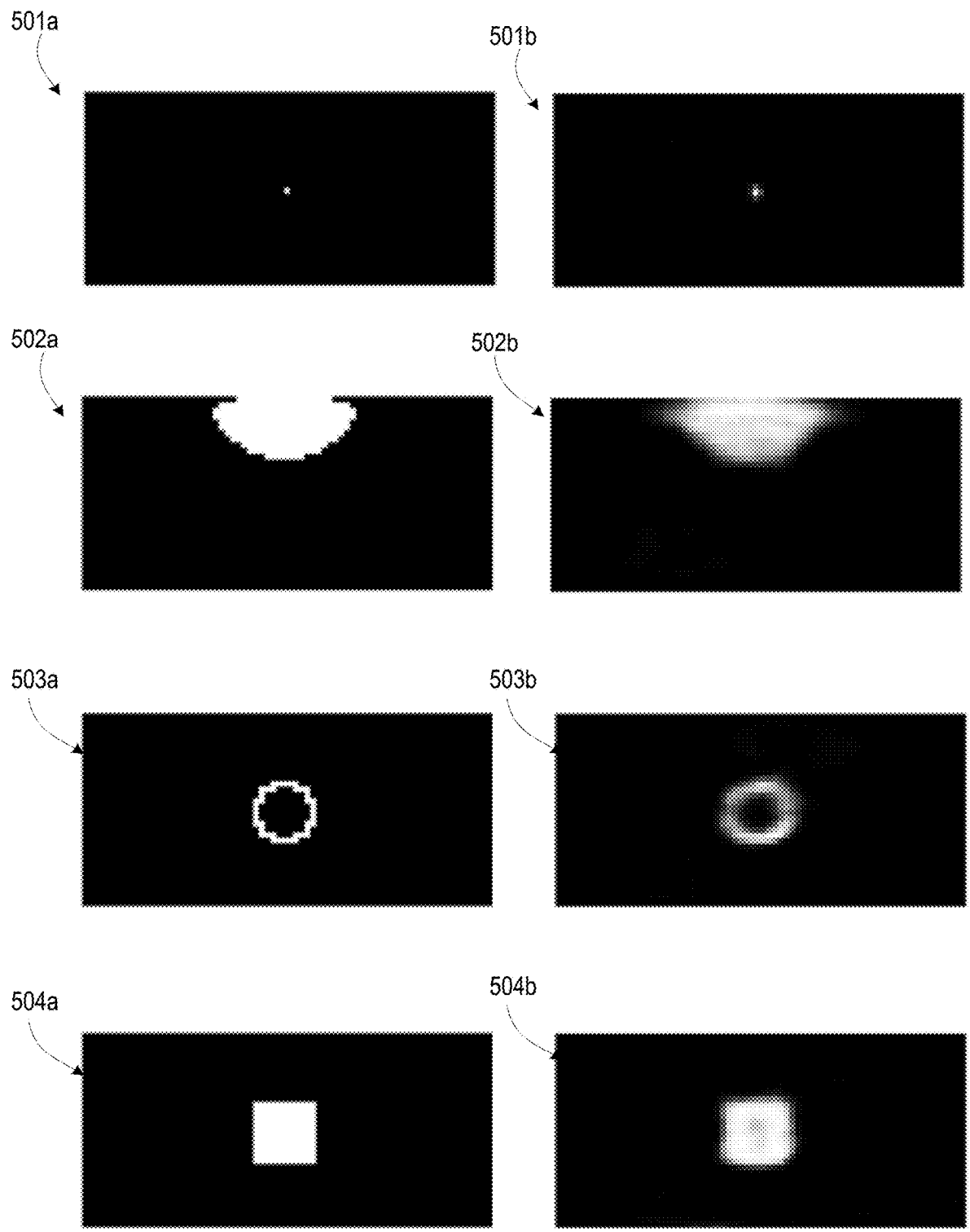
FIG. 5 contains simulated source distributions and the corresponding reconstructed images for one embodiment of the present disclosure.

FIG. 5 depicts four (4) simulated source distributions 501a-504a and corresponding ReGeNN training reconstructions 501b-504b respectively for a point, a circle deformed by the polar-to-2D representation, a ring, and a solid square. The present innovation using a ReGeNN reproduced the images with high accuracy and resolution for all source sizes and directions.

Figure 6:
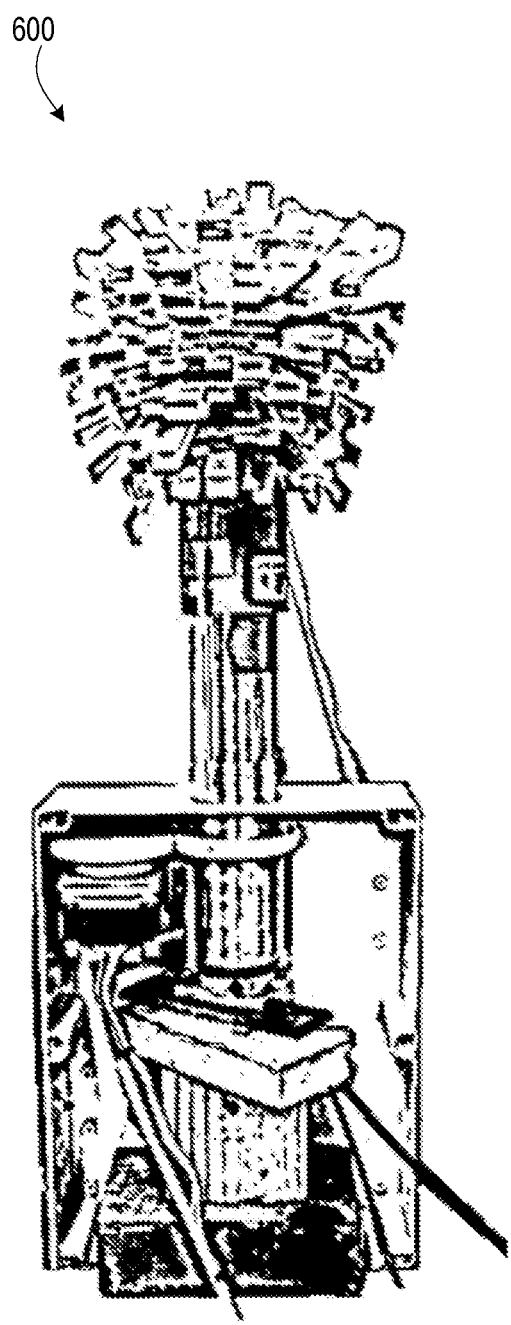
FIG. 6 contains an image of an experimental identification system that utilizes an Eigenvector-based scatter mask, according to one or more embodiments.
Figure 7:
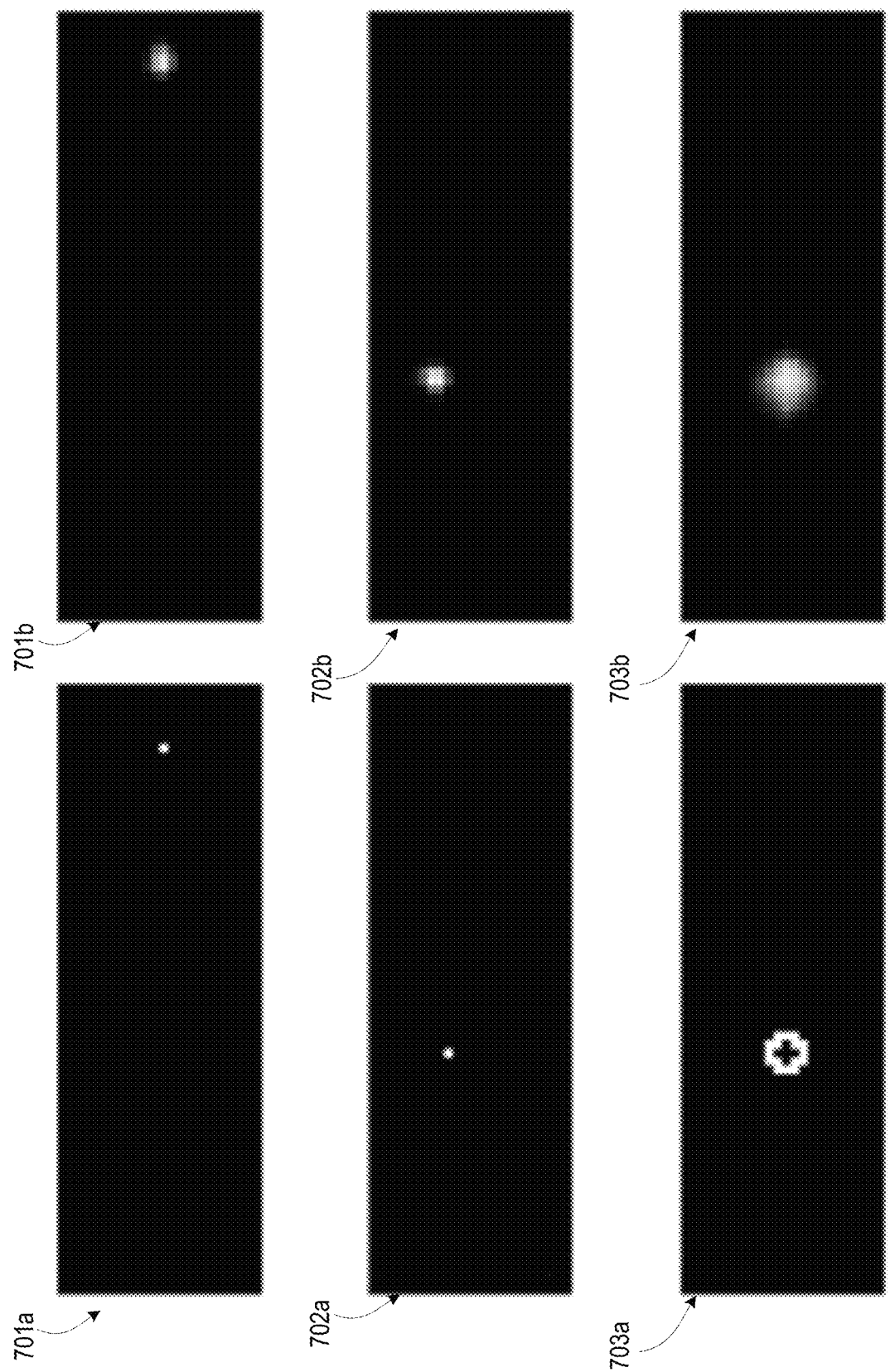
FIG. 7 contains the reconstructed image obtained by using ReGeNN and the experimental setup of FIG. 6, according to one or more embodiments.

FIG. 6 shows an experimental setup with one embodiment of the present innovation and a $^{22}$Na gamma emitter as the source. Three sources distributions were measured using this system 600 and reconstructed using a ReGeNN-based algorithm. Three source distributions 701a-703a and their corresponding reconstructions 701b-703b are depicted in FIG. 7 for a first point, a second point at another location, and a ring. The relative direction and size were predicted to within five degrees of the true distributions, with excellent noise suppression in the reconstructions, indicating accurate images of the sources' spatial distributions were obtained.

The Eigenvector RSM produced less degenerate DRCs than FitzGerald's RSM. By addressing this issue, the invention and corresponding ReGeNN enables radiation imaging to occur. Simulated and experimental results demonstrate that the present invention can accurately resolve complex, noisy source shapes, while avoiding the phantom sources and image artifacts that occurred with FitzGerald's design.

Figure 8:
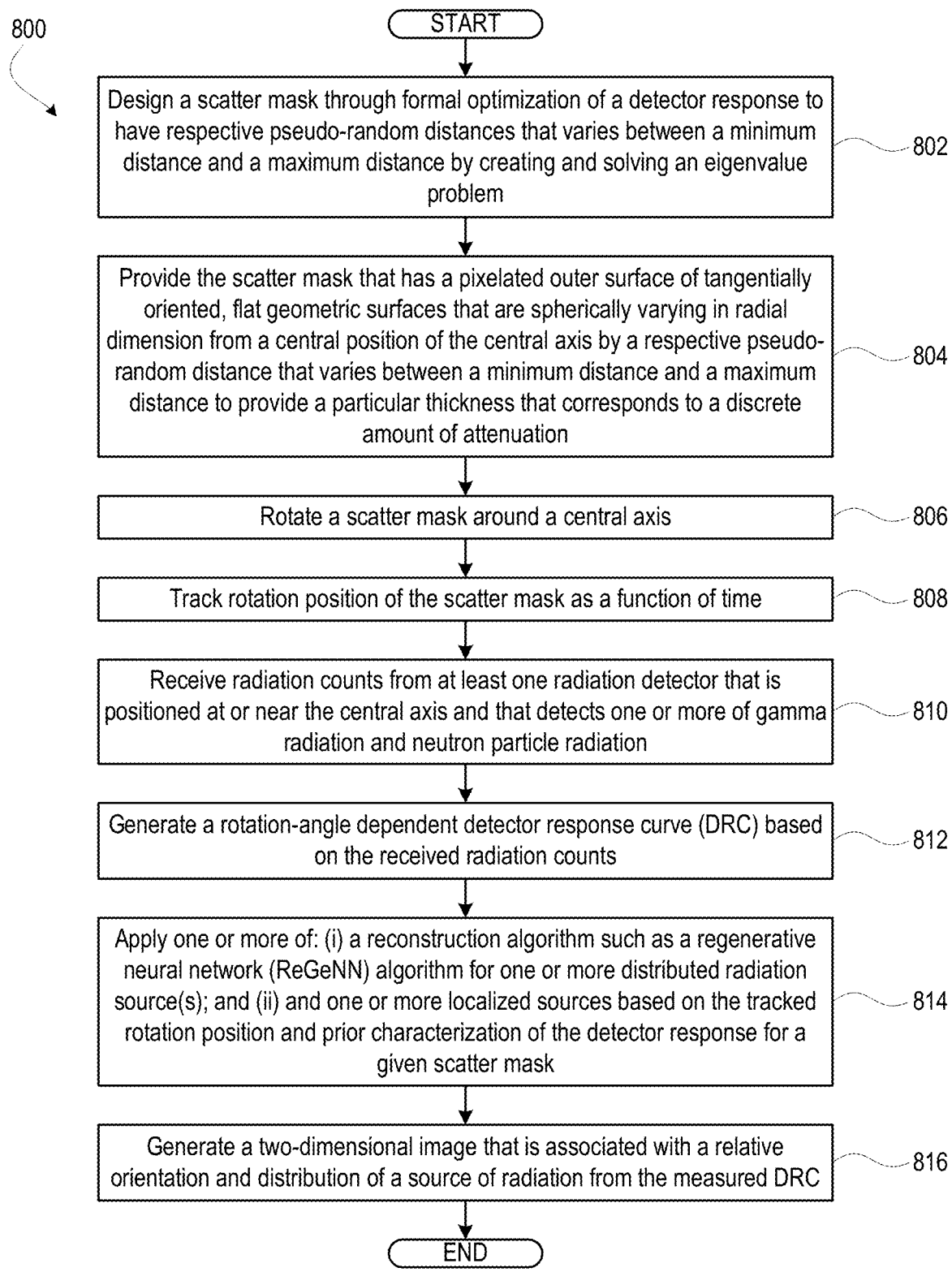
FIG. 8 presents a flow diagram of a method for imaging a distributed source of radiation from an unknown direction, according to one or more embodiments.

FIG. 8 presents flow diagram of a method 800 for imaging a distributed source of radiation from an unknown direction. Method 800 can be performed by components described above for FIGS. 2A-2C, 3A-3B, 4A-4C, and 5-7. For clarity, method 800 includes designing and producing an innovative RSM for use in the imaging according to aspects of the present disclosure. In one or more embodiments, method 800 includes designing a scatter mask through formal optimization of a detector response to have respective pseudo-random distances that varies between a minimum distance and a maximum distance by creating and solving an eigenvalue problem (block 802). Method 800 includes producing the scatter mask that has a pixelated outer surface of tangentially oriented, flat geometric surfaces that are spherically varying in radial dimension from a central position of the central axis by a respective pseudo-random distance that varies between a minimum distance and a maximum distance to provide a particular thickness that corresponds to a discrete amount of attenuation (block 804). Method 800 includes rotating a scatter mask around a central axis (block 806). Method 800 includes tracking rotation position of the scatter mask as a function of time (block 808). Method 800 includes receiving radiation counts from at least one radiation detector that is positioned at or near the central axis and that detects one or more of gamma radiation and/or neutron particle radiation (block 810). Method 800 includes generating a rotation-angle dependent detector response curve (DRC) based on the received radiation counts (block 812). Method 800 includes applying one or more of: (i) a reconstruction algorithm such as a regenerative neural network (ReGeNN) algorithm for one or more distributed radiation source(s); and (ii) one or more localized sources based on the tracked rotation position and prior characterization of the detector response for a given scatter mask (block 814). Method 800 includes generating a two-dimensional image that is associated with a relative orientation and distribution of a source of radiation from the measured DRC (block 816). Then method 800 ends.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

In the preceding detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method for imaging a distributed source of radiation from an unknown direction, the method comprising:
   rotating a scatter mask around a central axis, wherein the scatter mask has a pixelated outer surface of tangentially oriented, flat geometric surfaces that are spherically varying in radial dimension from a central position of the central axis by a respective pseudo-random distance that varies between a minimum distance and a maximum distance to provide a particular thickness that corresponds to a discrete amount of attenuation;
   tracking rotation position of the scatter mask as a function of time;
   receiving radiation counts from at least one radiation detector that is positioned at or near the central axis and that detects one or more of gamma radiation and neutron particle radiation;
   generating a rotation-angle dependent detector response curve (DRC) based on the received radiation counts;
   applying one or more of: (i) a reconstruction algorithm for one or more distributed radiation source(s); and (ii) one or more localized sources based on the tracked rotation position and prior characterization of the detector response for a given scatter mask; and
   generating a two-dimensional image that is associated with a relative orientation and distribution of a source of radiation from the measured DRC.

2. The method of claim 1, wherein the scatter mask has the pixelated outer surface of tangentially oriented, flat geometric surfaces that are spherically varying in radial dimension from the central position of the central axis by the respective pseudo-random distance that varies between the minimum distance and the maximum distance to provide the particular thickness that corresponds to a discrete amount of attenuation that maximizes the radiation image information encoded as determined through formal optimization of the detector response.

3. The method of claim 1, wherein applying the reconstruction algorithm comprises applying a regenerative neural network (ReGeNN) algorithm.

4. The method of claim 1, further comprising creating the scatter mask to have the respective pseudo-random distances that varies between a minimum distance and a maximum distance by creating and solving an eigenvalue problem.

5. A radiation imaging system that images distributed and localized sources of radiation from an unknown direction, the radiation imaging system comprising:
   a scatter mask having a pixelated outer surface of tangentially oriented, flat geometric surfaces that are spherically varying in radial dimension from a central position of a central axis by a respective pseudo-random distance that varies between a minimum distance and a maximum distance to provide a particular thickness that corresponds to a discrete amount of attenuation;
   at least one radiation detector that is positioned at the central axis and that detects one or more of gamma radiation and neutron particle radiation;
   a rotation system to rotate the scatter mask around the central axis; and
   a controller that is communicatively coupled to the at least one radiation detector and the rotation system and which:
      tracks rotation position of the scatter mask as a function of time,
      receives radiation counts from at least one radiation detector that is positioned at or near the central axis and that detects one or more of gamma radiation and neutron particle radiation,
      generates a rotation-angle dependent detector response curve (DRC) based on the received radiation counts,
      applies one or more of: (i) a reconstruction algorithm for one or more distributed radiation source(s); and (ii) one or more localized sources based on the tracked rotation position and prior characterization of the detector response for the scatter mask, and
      generates a two-dimensional image that is associated with a relative orientation and distribution of a source of radiation from the measured DRC.

6. The radiation imaging system of claim 5, wherein the scatter mask has the pixelated outer surface of tangentially oriented, flat geometric surfaces that are spherically varying in radial dimension from the central position of the central axis by the respective pseudo-random distance that varies between the minimum distance and the maximum distance to provide the particular thickness that corresponds to a discrete amount of attenuation that maximizes the radiation image information encoded as determined through formal optimization of the detector response.

7. The radiation imaging system of claim 5, wherein the reconstruction algorithm comprises a regenerative neural network (ReGeNN) algorithm.

8. The radiation imaging system of claim 5, wherein the scatter mask is designed to have the respective pseudo-random distances that varies between the minimum distance and the maximum distance by creating and solving an eigenvalue problem.

* * * * *